United States Patent [19]

Vaillancourt

[11] Patent Number: 4,725,267
[45] Date of Patent: Feb. 16, 1988

[54] POST-INJECTION NEEDLE SHEATH

[76] Inventor: Vincent L. Vaillancourt, 14 Bunyan Dr., Livingston, N.J. 07039

[21] Appl. No.: 46,569

[22] Filed: May 6, 1987

[51] Int. Cl.⁴ .............................................. A61M 5/32
[52] U.S. Cl. .................................... 604/192; 604/198; 604/263
[58] Field of Search ............... 604/198, 192, 263, 110, 604/111, 162, 163

[56] References Cited

U.S. PATENT DOCUMENTS

| 3,134,380 | 5/1964 | Armao | 604/198 |
| 4,564,054 | 1/1986 | Gustausson | 604/198 X |
| 4,664,654 | 5/1987 | Strauss | 604/198 |

Primary Examiner—John D. Yasko
Attorney, Agent, or Firm—Ralph R. Roberts

[57] ABSTRACT

A post-injection needle sheath for enclosing the sharpened end of a needle used with a syringe is shown with and without spring actuation. This sheath is initially in a compact and secured condition on the needle hub and has a substantial portion of the needle exposed for insertion into a patient or vial. Two embodiments employ a compression spring. Three embodiments avoid a spring per se, but have a corrugated portion and a flange portion that are manipulated by an attendant to urge the sheath forward to enclose the sharpened end of the needle. In all embodiments, the forward end includes a transverse wall in which is formed an aperture that is slightly larger than the shank of the needle. Protection to the exposed needle before use is provided by a conventionally removeable shield which is removed at time of use. After withdrawal of the needle from the patient, the sheath, with the cap or end portion, is moved forward to enclose the sharpened needle.

20 Claims, 12 Drawing Figures

POST-INJECTION NEEDLE SHEATH

BACKGROUND OF THE INVENTION

1. Field of the Invention

With respect to the field of the invention as established in and by the U.S. Patent Office, this invention is believed to be found in the general class entitled "Surgery," and particularly in the subclasses thereof directed to protectors for the tips of needles used with hypodermic syringes.

DESCRIPTION OF THE PRIOR ART

Needle protectors are well known and have been in use for many years with the needles used with hypodermic syringes. Conventionally, needles are made with hubs and sockets adapted to be attached to the reduced end of a syringe. A molded plastic cap is conventionally removeably secured to the hub of the needle. After mounting the needle on the syringe, the cap is removed to expose the needle for use.

Accidental needle stick injuries are extremely common in health care workers, such as nurses, physicians, laboratory workers an housekeeping personnel. Needle stick exposures can result in transmission of hepatitis B, non A non B hepatitis, and potentially, the acquired immune deficiency syndrome—AIDS, or other transmissible diseases. The health hazards associated with needle stick injuries are of greater risk for health care workers in the 1980's than ever before.

Accidental needle sticks often occur when a blood drawer attempts to recap a needle after use or leaves a contaminated needle exposed on work surfaces where the blood drawer or other workers accidentally impale themselves.

A modification of the current vacuum tube phlebotomy system is urgently needed to provide a protective barrier between health care workers and exposed, contaminated needles.

It is well known that used hypodermic needles are extremely susceptible to transmitting diseases. Hepatitis and other highly contagious diseases can be transmitted by successive use of the same needle by different individuals. In a hospital environment, however, precautions are taken to avoid use of contaminated needles by their expeditious disposal. Problems exist, however, in storing the needle for disposal and commonly the protective cap associated with the needle receives the used needle for discarding. However, it is apparent that the bore of the needle cap is dimensioned not much larger than the diameter of the needle and its needle base which removeably attaches to a syringe. Misalignment of the needle with respect to the cap when trying to reinsert the needle therein can cause the hand which holds the cap to be punctured, thereby increasing the liklihood of transmission of a contagious disease.

U.S. Pat. Nos. 2,847,995 to ADAMS as issued Aug. 19, 1958, and 3,134,380 to ARMAO as issued May 26, 1964 are representative of shields used with hypodermic needles in which the shield or protector is adapted to be accordionized for use and then expanded to cover the tip of the needle. This type of needle-tip protector is contemplated to be mounted on the syringe or at least the needle hub and remain in a mounted condition during use. With the rapid increase in the AIDS-infected and human carriers, there has been a concentration of providing needle protection. U.S. Pat. No. 4,592,744 to JAGGER et al as issued June 3, 1986 provides a specially constructed hub and a self-sheathing assembly. Devices similar to this are known to the art and are utilized to provide a protecting extending flange secured to or as a portion of the tubular cap which is to be reinstalled to cover the needle. Shielded protectors which anticipate flanged extensions are numerous and have recently been promoted and/or offered as a protector of the attendant.

Also known are needle-tip protectors which anticipate attendant manipulation. Representative of these manipulable devices are U.S. Pat. No. 2,876,770 as issued to WHITE on Mar. 10, 1959; U.S. Pat. No. 2,925,083 as issued to CRAIG on Feb. 16, 1960, and U.S. Pat. No. 3,306,290 as issued to WELTMAN on Feb. 28, 1967.

In the above-noted patents and as far as is known, there is a protector that is mounted on the needle and is in a stored and compressed condition and at the initial stage of use provides an exposed needle and, after withdrawal from the patient, provides a needle-tip protector to prevent unwanted and accidental pricking of the attendant by this needle tip. These patents showing needle protectors with spring means and manipulable actuation are expensive and contemplate rigid shield members. The present invention is adapted for use with the disposable syringes now used and with the sharp needle tip being protected substantially immediately, when withdrawal from the patient is made.

SUMMARY OF THE INVENTION

This invention may be summarized, at least in part, with reference to its objects. It is an object of this invention to provide, and it does provide, a needle-tip protector for a sharpened needle carried on a disposable syringe or blood aspirator.

It is a further object of this invention to provide, and it does provide, a post-injection needle sheath in which the sharpened needle is initially covered by a removeable needle shield and, after removal of said shield, the needle is exposed for insertion into the patient, after which a nose member is caused to be moved forward beyond the sharpened end of the needle and remain there so as to prevent unwanted pricking of the attendant.

It is a further object of this invention to provide, and it does provide, a needle cap or nose member that is moved into a sharpened end protection by means of a compression spring. This needle cap is retained in a rearward position by a friction locking means.

It is a further object of this invention to provide, and it does provide, a needle cap or nose member that is moved into a sharpened end protection by means of a compression spring. This needle cap is retained adjacent the needle hub by a lock means with a release provided by a small rotating manipulation.

It is still a further object of this invention to provide, and it does provide, a needle cap or nose member attached or integral with a convoluted, corrugated or bellows material, and preferably this material has a memory. This material is adapted to be secured to the hub of the needle, the nose cap having an aperture for the passage of the needle, and with said cap having a manipulative flange and a forward contour adapted for removeable retention of a needle shield. This post-injection needle sheath is disposed to expose the needle for usual use after the shield is removed, and after use the needle sheath is pushed forward to enclose the sharpened end of the needle. The nose portion may be of rigid plastic or may be of a partially resilient material.

It is still a further object of this invention to provide, and it does provide, a needle cap or nose member integral with a bellows of a material that may have a memory, said cap having a shallow, disc-like configuration having a through aperture that is slideable on the needle, and with a protruding portion configured to provide a seating means for removeably retaining a needle shield. This sheath has a manipulative flange for moving forward the disc-like forward portion and the rear of the bellows portion is secured to a reduced nose portion of the syringe.

It is still a further object of this invention to provide, and it does provide, a post-injection needle sheath for attachment to the hub of a needle, with said sheath having a nose portion with a formed forward-end portion whose outer configuration is adapted to receive and removeably retain a needle shield. A flange is provided on said nose portion to assist the attendant in manipulation. This nose portion has an aperture therethrough for sliding on the shank of the needle, and on the internal-end surface of this nose portion there is formed a deflection portion for insuring that the sharpened end of the needle moves away from an alignment with the through aperture. A bellows portion is attached to the nose portion and to the needle hub above or rearward of molded flutes in the needle hub. The nose portion also is internally formed with flutes sized and adapted to mate with and slide by the flutes formed on the needle hub.

In brief, this post-injection needle sheath is contemplated to be used with a needle hub of conventional construction and carrying a needle of conventional size and length. The needle hub may be with a known taper or with a luer lock. The sheath in initial condition is secured so that the needle is in an exposed condition and with means for removeably securing a needle shield of conventional construction. Five embodiments are shown, two of which employ compression springs which are used to move and maintain nose portions in a needle-enclosed condition until and when the needle and hub are discarded. This post-injection needle sheath is believed to be inexpensive and, as used, to prevent accidental pricking of the attendant after needle withdrawal from a patient.

In two embodiments, to be shown and described hereinafter, a needle cap constructed of molded plastic is used with compression springs. The needle cap members are secured to a needle hub so as to expose the sharpened needle for conventional use. A needle shield is removeably mounted on the spring-actuated needle cap to protect the sharpened needle and maintain sterility until time of use. In one embodiment, the needle cap and spring are maintained in a stored condition by means of a friction fit with a partially resilient tubular member. Manipulation by the attendent allows the compressed spring to move the cap cover forward to cause the sharpened end of the needle to be enclosed. In the alternate construction, a washer lock is secured to the needle hub and the needle cap is provided with mating lug portions so that in one position the apparatus is secured by this lock arrangement, and with a small rotation the spring and cap are released and allowed to move forwardly to a protector condition and the sharpened end is in an enclosed condition.

In another embodiment, an accordionized portion providing a bellows is attached to a nose portion having a protruding configuration shaped to removeably receive and retain a needle shield. The rear or inner end of the bellows is secured to a needle hub and the other end is attached to the nose cap, which may have a manipulable flange. This nose portion is provided with an aperture sized to provide a slideable means for the movement along the shank of the needle. The bellows portion may have memory providing a spring action tending to draw the nose portion toward the sharpened end of the needle. In an alternate embodiment, the nose portion may be made of a resilient or semi-resilient material tending to imbed the sharpened end of the needle in the transverse inner end wall of the nose portion of the nose member.

In yet another alternate embodiment, the bellows apparatus is used with a luer lock syringe. This bellows portion has a rearwardly-extending skirt that is secured to the nose portion of the syringe. In yet another alternate embodiment, the bellows portion is secured to the molded hub of the needle and the nose portion of the needle sheath is anticipated to be made of plastic, with the bellows portion integral with or attached to a nose portion. This bellows portion is comtemplated to have memory so that when the nose portion is moved along and past the needle end, this sharpened end is conventionally retained in the inner area of this nose portion. The hub of the needle is adapted to be used with a luer lock.

In yet another embodiment, the nose or cap is shown with flutes adapted to mate with flutes conventionally provided with molding the hub of the needle. This mating of the flutes on the hub and the nose portion of the sheath is disposed to provide rotation of the needle hub for seating the hub in a taper or a luer lock. The bellows portion may or may not have memory so that when manipulated into a needle-protecting position, there may or may not be an exertion of pressure for the end of the needle to be retained in the inner end of the nose portion. This embodiment particularly is to provide ready rotative motion for mounting of the needle sheath on a syringe.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there have been chosen specific embodiments of the post-injection needle sheath as adopted for mounting on a needle used with a syringe and showing preferred means for making said needle sheath for a one-time use, and when the sheath is in a protecting condition needle pricking is eliminated. These specific embodiments have been chosen for the purposes of illustration and description as shown in the accompanying drawings wherein:

BRIEF DESCRIPTION OF THE DRAWINGS

FIGS. 1A, 1B and 1C represent side views, partly diagrammatic, of a spring-actuated cap that is released and moved to enclose a sharpened end of a needle, wherein FIG. 1A is a side view, partly in section, and in condition for attachment to a syringe, with a standard needle shield removeably secured to provide protection and sterility of this needle prior to use;

FIG. 1B is the spring-actuated cap or nose portion as constructed for mounting to a needle hub and prior to use of the needle, and FIG. 1C is a side view, partly diagrammatic, and showing the post-injection apparatus in an expanded condition, with the cap or nose portion moved past the sharpened end of the needle into protective condition;

FIGS. 2A, 2B and 2C represent side views, partly diagrammatic, of a spring-actuated cap similar to the device of FIGS. 1A, 1B and 1C, but with a lock arrangement that is adapted for release with a manipulative rotation of the cap in relation to the needle hub, wherein FIG. 2A is a side view of a needle and hub of conventional configuration before securing of the washer lock to said hub; FIG. 2B is a side view, partly diagrammatic, and in section, of the spring-actuated sheath in a closed condition so that the needle is in exposed condition for insertion into the patient, and FIG. 2C is a side view, partly diagrammatic, and in section, with and when the cap is turned to a release condition and the cap moved to a needle-end enclosed protective position;

FIGS. 3A, 3B, 3C and 3D represent side views of an alternate post-injection needle sheath absent a spring member, wherein FIG. 3A is a side view of the sheath in an assembled condition and as shipped, stored and ready for use; FIG. 3B is a side view of the sheath of FIG. 3A, but with the bellows and front nose portion in section to diagrammatically show the association and spacing from the needle and hub; FIG. 3C represents the side view of the sheath of FIG. 3B, but with the bellows portion in the forward and expanded condition and partly in section to depict the sharpened end of the needle now protected by the nose portion of the sheath, and FIG. 3D is a fragmentary, sectional side view of an alternate nose construction wherein the nose portion is made from a partially resilient material;

In the following description and in the claims, various details are identified by specific names for convenience. These names are intended to be generic in their application. Corresponding reference characters refer to like members throughout the several figures of the drawings.

The drawings accompanying, and forming part of, this specification disclose details of construction for the purpose of explanation, but structural details may be modified without departure from the concept and principles of the invention and the invention may be incorporated in other structural forms than shown.

DESCRIPTION OF THE EMBODIMENT OF FIGS. 1A, 1B AND 1C

Figure 1A:
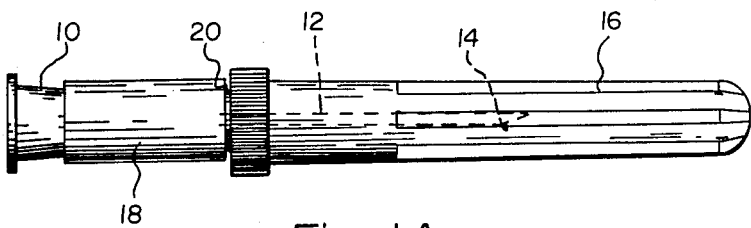
Figure 1B:
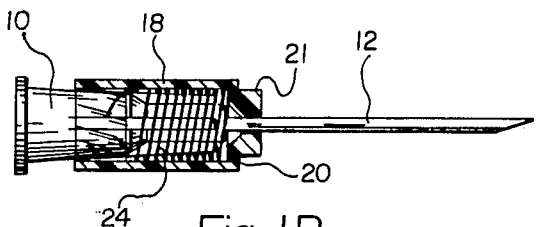
Figure 1C:
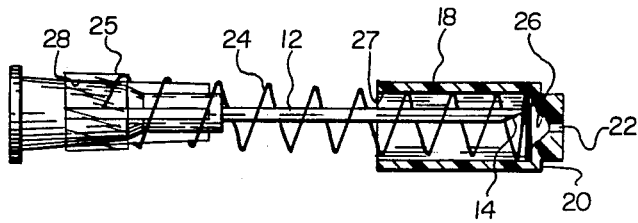

Referring next to the drawings and, in particular, to the embodiment diagrammatically shown in FIGS. 1A, 1B and 1C, a hypodermic syringe (not shown and conventional) has an end adapted to receive and retain a hub 10 carrying a secured needle 12. This needle has its distal end 14 sufficientlly sharpened to enter the skin of a patient. A standard needle shield or cap 16 is provided for this assembly. This shield is usually a molded member adapted to protect the attendant from pricking his or her finger and to avoid potential contamination during transport and prior to use. A separate assembly is provided in which a formed cap member 18 has a shoulder 20 having an external molded step 21 which is sized to receive and retain the shield 16. This cap member is generally tubular, with the shouldered end substantially closed except for a through passageway 22 which is a few thousandths of an inch greater in diameter than the outer diameter of the shank of needle 12. This greater diameter allows a freely sliding fit of the cap 18 on and along the shank of the needle 12. A compression spring 24 has an inner end 25 adapted to engage the end of the hub 10 and the other end to engage the inner end surface 26 of the tubular interior of the cap 18.

In FIG. 1A, the device described above is shown in condition for attachment to a syringe. (If stored or shipped, it requires an overpackage to retain sterility.) The conventional needle and hub 10 are shown with cap 18 mounted on the hub. The cap 18 has the contoured shoulder 20 or the like to provide friction mounting on said hub. The securing may include a friction fit (heat-seal), a lock, or may include adhesive. The needle cap 18 is removeably secured to the hub 10, with this cap and spring 24 disposed of with the needle 12 after use. The shield 16 is shown in mounted position and the spring 24 is in closed position. The cap 18 is in mounted condition. If desired, a tubular member 28 providing a tight securing fit between the inner bore 27 of cap 18 and the hub 10 may be provided.

In FIG. 1B, the assembly is depicted in the condition of FIG. 1A, but with the needle shield 16 removed so that the needle is exposed. Conventionally, the needle is inserted through a resilient stopper and the syringe is aspirated to draw into the barrel of the syringe the medication to be used. The spring 24 is in the compressed condition and remains in such condition during use of the needle and until withdrawal from the patient. A urethane tubing 28 is depicted in this view and provides a securing fit with the inner bore 27.

In FIG. 1C, the apparatus of FIG. 1A is shown after withdrawal of the needle 12 from the patient. The needle cap 18 is dislodged manually from the hub 10. As and when released, the spring 24 urges cap 18 outward to the free length of the spring. This free length is contemplated to be sufficient for the needle cap 18 to extend, as shown, whereat the sharpened tip end 14 of the needle is within the cap 18. The hole 22, although a slide fit on the shank of needle 12 after passing the tip end 14, is not aligned for reinsertion. Even if the cap is urged toward the hub of the needle, the sharpened end is engaged by the inside-end surface portion 26 of the cap.

EMBODIMENT OF FIGS. 2A, 2B AND 2C

The post-injection needle sheath apparatus is shown in this embodiment with alternate cap-securing means. In FIG. 2A, the standard needle hub 10 as in FIG. 1 A is depicted, and extending therefrom is the needle 12 having a sharpened end 14. Rather than a friction fit for retaining the cap to the hub as in FIG. 1A, there is provided a locking device.

Figure 2B:
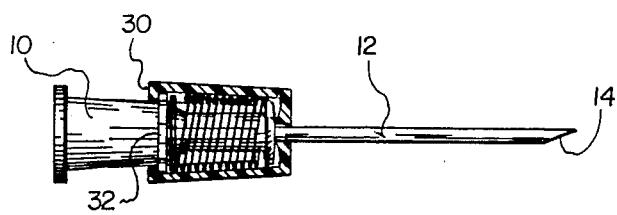
Figure 2A:
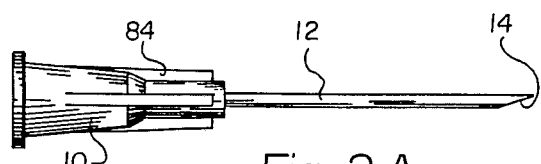
Figure 2C:
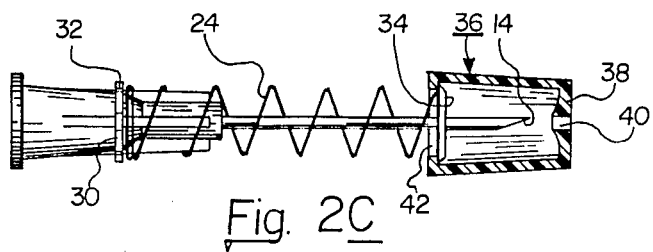

In FIGS. 2B and 2C, a washer lock, identified as 30, has a plurality of protruding ears or tabs 32. This member 30 is secured to the midlength (or above) of hub 10. A compression spring 24, like or very similar to that shown in FIGS. 1A, 1B and 1C, is mounted on the needle and, as depicted, has the inner end slideable on the smaller portion of the hub 10. The other end of spring 24 is secured to a tapered disc 34. A needle cap, generally identified as 36, is a hollow molding and is contemplated to be substantially tubular. An outer-end wall of plastic is identified as 38 and includes an aperture 40 which is slightly larger in diameter than the shank of the needle 12 used therewith. The other (inside) end of the cap member 36 is formed with a through aperture 42 which not only freely passes the spring 24, but is also scalloped to provide inwardly-extending lug portions to mate with and retain the extending tabs 32 of the washer 30.

Any bayonet lock device will perform this lock securement and release. It is contemplated that a small rotative action such as a quarter turn will release the needle cap 36 to progress outwardly.

In FIG. 2C, the cap 36 has been moved outwardly by the bias of and in spring 24. The disc 34 provides a stop to the excess outward motion of the cap 36. The inner contour on end 38 is designed to prevent the sharpened end 14 of the needle from reentering aperture 40.

In FIGS. 1A, 1B, 1C, 2A, 2B and 2C, the post-injection needle sheath is shown with a spring 24 which is utilized so as to provide a force for moving a cap member to a determined outer position. The spring member usually is made of steel as this is believed to be the least expensive, but this is not to preclude making of other materials. Whether the spring is secured to the forward end portion of hub 10 or is otherwise attached, it is contemplated that the spring end at or on the hub be secured so that accidental dislodgement does not occur. In like manner, the outer end of said spring is adapted to prevent unwanted separation of the cap and associated protective apparatus.

EMBODIMENT OF FIGS. 3A, 3B, 3C AND 3D

In FIGS. 3A, 3B, 3C and 3D, yet another embodiment of a post-injection needle sheath is shown. Like the prior embodiments shown and discussed, this alternate apparatus has the needle initially exposed, and through and with manipulative means the protective nose cap is moved by the attendant after the needle is withdrawn from the patient. The needle hub 10 is like or identical to that shown above.

Figure 3A:
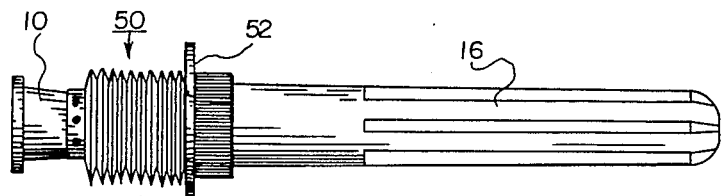

To the needle hub 10, as seen in FIG. 3A, is attached a bellows-type member, generally identified as 50, having a finger guard 52. This member 50 is so configured that a conventional needle shield 16 (as above) may be removeably mounted. This shield is conventional and of molded plastic, and is similar to that shown or often is of a slightly differing tubular shape. The shield is utilized to prevent the needle and sharpened end to be exposed until time of use. The member 50 has a flange end or lip 54 that is secured to the hub of the needle. This securement may be by adhesive, heat-sealing, welding or a mechanical fit.

Figure 3B:
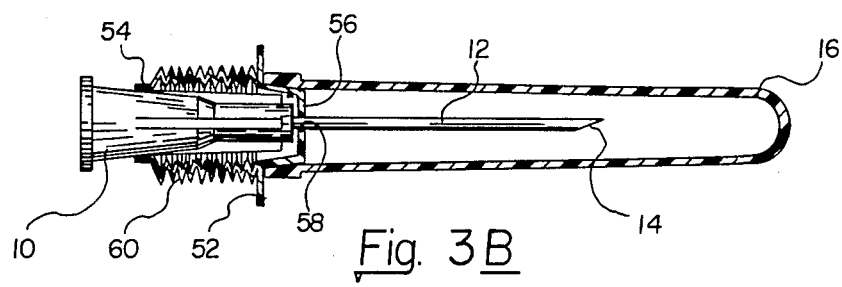

In FIG. 3B, the bellows-type device 50 is shown in a diagrammatic sectional view so as to depict the several essential members. This view is enlarged to illustrate the interrelationship of the associated parts. The shield 16 is removeable and at time of use is removed, exposing the needle 12. The finger guard 52 may be grasped during the separation of the guard 16 from the member 50. The finger guard 52 is made with a nose portion, identified as 56, in which an aperture 58 is formed. This aperture is slightly larger than the shank portion of the needle 12 so as to provide a free sliding fit therealong. A corrugated-bellows portion 60 is shown as integrally formed with and as the nose 56 and guard 52 are molded. Plastic may be formed with such bellows configuration by many known methods and no patentable aspects are directed to this method, but the use in and with the remainder of member 50 is believed novel. It is to be noted that forming the nose portion 56, a shoulder portion is provided which is sized to receive and removeably retain said shield 16.

Figure 3C:
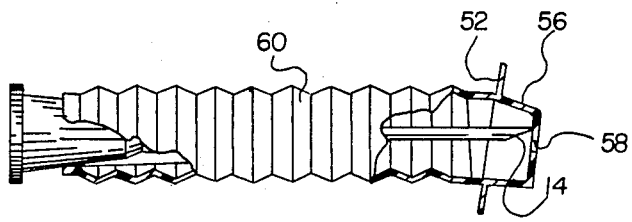

In FIG. 3C, the device of FIG. 3B is shown with the shield 16 absent and with the needle 12 now withdrawn from the patient. The bellows portion 60 is now in the expanded condition, having been moved forwardly (rightward) by the attendant. It is anticipated that finger guard 52 may be utilized for the forward manipulation. It is to be particularly noted that nose portion 56, after sliding along the needle, passes the sharpened end 14 and this sharpened end enters and is retained within the nose portion 56. This expanded sheath of FIG. 3C remains on the needle in this attitude until the needle is destroyed, generally by placing it in a sharp cutter. The aperture 58 is only a few thousandths of an inch larger than the needle 12 and, after the nose 56 passes the sharpened end 14, is sufficiently misaligned so the tip and needle do not again enter aperture 58.

Figure 3D:
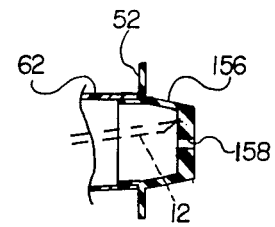

In FIG. 3D, an alternate is provided to the making of at least the nose portion 56. Rather than using a rigid plastic, a resilient material, such as rubber, is used. This resilient nose portion is identified as 156. The finger guard 52 may be an integral portion or may be a flange ring secured by adhesive or other means. As depicted, the bellows portion 60 shown in FIG. 3C is made with an end portion 62 that is slideable on the nose portion 156 and is secured thereto by adhesive or like means. The rubber nose portion also has an aperture 158 similar to 58 and sized to provide a slide fit on the shank of the needle. The use of rubber or a resilient material allows the sharpened end of the needle to enter the end of the nose sufficiently so as to preclude movement from the initially engaged location. The forming of the nose member 156 of resilient material often causes a frictional engagement with the shank of the needle as it is advanced so that, after passing the sharpened end 14, this end is retained in and within the interior cavity formed in the nose portion 156. It is contemplated that this entire assembly, bellows 62 and cap 156 may be molded from an elastomeric material.

EMBODIMENT OF FIG. 4

Figure 4:
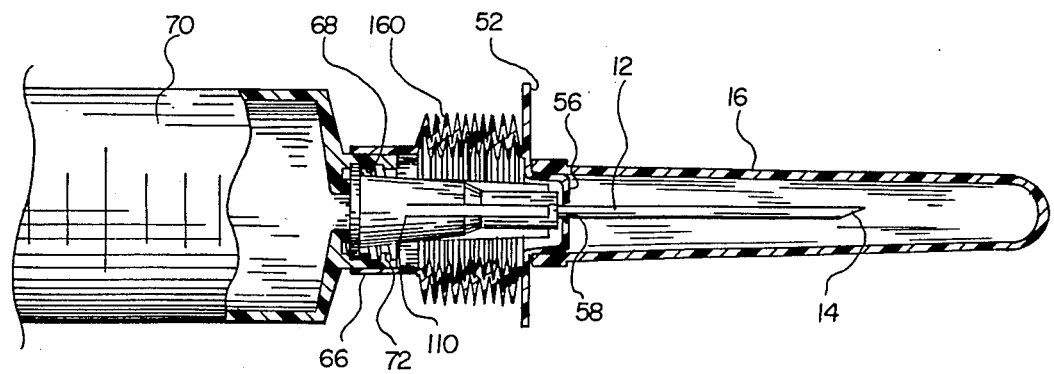
FIG. 4 represents a side view, partly diagrammatic, and in section, showing yet another alternate configuration and construction in which the bellows portion has a rearwardly-extending tubular portion adapted to be secured to the extending reduced end portion of the syringe so that the needle and hub may be mounted separately to the syringe.

In FIG. 4 is shown a modification of the concepts or the apparatus of FIGS. 3A, 3B and 3C. The shield 16 is conventional and, as above, is adapted to be removeably retained on the inner stepped portion of the nose portion 56 as shown in FIG. 3B above. Aperture 58 is also formed therein and the bellows portion extends from the finger guard flange 52. This bellows is identified as 160 to differentiate from the concept of FIG. 3B. Rather than having a sleeve portion 54, which in FIG. 3B is sized to be and is secured to the hub portion 10, this sleeve portion (which is identified as 66) is sized to slide on the extending forward end portion 68 of a syringe 70. This syringe 70 is conventional and has a luer lock (female) capability 72 to receive and retain a luer lock hub 110 in which needle 12 is secured therein. It is to be noted that sleeve portion 66 may be secured to forward portion 68 as by heat-welding, ultrasonics or the like. In secured condition, the bellows portion 160 is expanded with and by the forward manipulation of the attendant.

Assembly of this unit may be achieved by securing the needle 12 and hub 110 in the luer lock 72. After mounting the bellows 160, the forward end 56 is slid onto and along the needle 12 to the position shown. The sleeve portion 66 is secured to forward-end portion 68 and then shield 16 is mounted on forward end 68 until time of use. At this time the shield 16 is removed, exposing the needle 12 and sharpened end 14. The syringe is conventionally aspirated, either for filling with drug or for withdrawing blood from the patient. It is to be noted that the needle is exposed until withdrawal from the patient, when the sheath is manipulated to provide sheath protection to the sharpened end 14 of the needle 12.

EMBODIMENT OF FIG. 5

Figure 5:
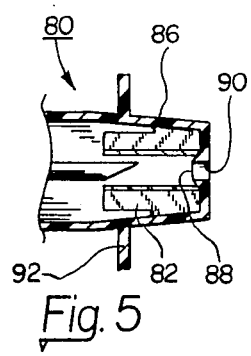
FIG. 5 represents a side sectional view of an alternate nose or cap member in which the cap may be used with structure of the corrugated portion and a needle as in FIG. 3C.

The fragmentary sectional view of FIG. 5 is contemplated to be used in and with a post-injection needle sheath, very similar to that shown and described above in FIGS. 3A, 3B, 3C and 3D. As with FIG. 3A, the corrugated portion, identified as 60, is secured to the hub 10 carrying the needle 12. This corrugated or bellows portion may or may not have memory and spring-back. The corrugated portion is identified as 60, and rather than having spring-back is contemplated to have little or no memory. The forward end or nose portion may be integrally formed of plastic or may be separately secured to this bellows or corrugated portion 60. This nose portion is identified as 80 and has a configuration similar to that seen in FIG. 3C. FIG. 5 is an enlarged scale and has the inner surface formed with flutes or ribs 82 adapted to mate with and to slide by and alongside ribs 84 (FIG. 2A) conventionally provided in and with the molding of hub 10. Needle 12, with sharpened end 14, is conventionally secured in and with the molding of hub 10. The forward end 86 of nose 80 is formed to accept and removeably retain a shield 16 as described above. It is to be noted that the interior of nose 80 is contoured inwardly at 88 to provide a sharpened needle and deflector means and so that aperture 90 is not aligned for reinsertion of the needle.

The flutes 82 in the nose portion 80 are utilized with engagement of flutes 84 on the needle hub so that the needle hub may be manipulated onto a forward end of a syringe. The syringe may be adapted to have a taper, in which case the hub 10 is advanced and rotated for seating. When and where the forward end of the syringe is provided with a luer lock, the needle hub 10 is as in FIG. 4 and the flutes 82 are matched with engaged flutes 84 on the hub 10 to insure that the hub 10 is rotated to mount the luer lock hub on the syringe. The bellows portion 60 is compressed as in FIG. 3A and shield 16 is in mounted condition. When the needle is to be used, the shield 16 is removed and the exposed needle used in the usual manner. After withdrawal of the needle from the patient, flange 92 is caused to be engaged and manipulated by the attendant so that the nose portion 80 is moved forwardly along the shaft of the needle 12 until sharpened end 14 passes through aperture 90. This sharpened end engages or may be embedded in the front inside wall 88. The expanded bellows portion 60 of FIG. 3C may or may not have memory, but with the nose portion pushed forward the sharpened end 14 and the entire needle are within the needle sheath. The bellows portion 60 is attached to the needle hub by adhesive, solvent, heat or friction means. The sheath apparatus is retained by the needle hub during use.

The bellows portion of FIGS. 3A, 3B, 3C, 3D, and 4 and 5 is contemplated to be used with a post-injection needle sheath protector. The bellows corrugations may be formed in a manner such as is provided for making drinking straws used in hospitals and the like. These drinking straws have these corrugations mechanically configured by known tooling, with a resulting corrugated portion that may be bent into a desired configuration and remains in this bent condition with little or no "spring-back." The bellows portions, shown and described above, with such properties may, when expanded, remain in the extended condition and the sharpened needle end thus is enclosed so as to avoid potential for needle pricking.

The post-injection needle sheath of FIGS. 1A, 2A, 3A and 5, like FIG. 4, may be configured so as to be attached to the nose portion 72 of the syringe 70 as in FIG. 4. The configurations showing the protector secued to the hub 10 are the preferred arrangement as the syringe may be of many designs and sizes. It is also to be noted that the sheath assemblies employing a corrugated or bellows portion also employ a flange portion 52 which is carried by the nose portion. The practitioner grasps the needle sheath in back (rearwardly) of the exposed needle and encloses the sharpened end by moving this nose portion along the needle. With this flange, the practitioner never exposes the hand, finger, etc., to this sharpened end, thus eliminating bell protectors as a means to prevent the practitioner from pricking.

The embodiments of FIGS. 2A through 5 have the nose or front portions depicted with a small taper, which taper is contemplated to provide seating and securing means for a needle shield 16. This shield is conventionally molded, with the configuration and size of the open end made commensurate with a nose or front portion of the provided needle sheath of this invention.

This post-injection needle sheath, as shown and described above, provides a novel method of construction and use. This post-injection needle sheath is particularly adapted for enclosing the sharpened end of a needle as used with a syringe, the needle in the originally presented condition having the sheath portion in a compact condition, with a substantial portion of the needle exposed for insertion into a vial or patient, this sheath, after needle use and withdrawal of the needle from the patient, manipulated so that said sheath is advanced, moving the forward cap portion so as to go beyond the sharpened end of the needle and enclose said sharpened end.

This method includes two means of constructing and moving the front-end closure. A spring is employed in two embodiments which include providing a compression spring adapted to be compressed so as to provide a force to urge said cap portion forwardly. Also disclosed is an embodiment which includes providing and securing one end of an intermediate tubular portion to the cap portion and having said intermediate portion convoluted or corrugated to form a bellows-like configuration portion, with the other end secured to the needle hub or syringe.

In all embodiments, the method includes:
 mounting an injection needle including a securing hub, a shank and a sharpened distal end, this hub adapted for removeable mounting on a closed end portion of a conventionally selected syringe;

forming and providing a cap portion having a forward end wall in which is formed a through aperture sized to slide on and along the shank of said needle;

limiting the forward movement of the cap portion as and when the sharpened end of the needle is within the cap portion so as to enclose said sharpened end to prevent accidental pricking, and retaining said sheath in needle-exposed condition until the attendant withdraws the needle from the patient and desires to enclose the sharpened end of the needle.

Terms such as "left," "right," "up," "down," "bottom," "top," "front," "back," "in," "out" and the like are applicable to the embodiments shown and described in conjunction with the drawings. These terms are merely for the purposes of description and do not necessarily apply to the position in which the post-injection needle sheath may be constructed or used.

While particular embodiments of the post-injection needle sheath have been shown and described, it is to be understood that the invention is not limited thereto and protection is sought to the broadest extent the prior art allows.

What is claimed is:

1. A post-injection needle sheath for enclosing the sharpened end of a needle as used with a syringe, the needle in the originally presented condition having the sheath portion in a compact condition, with a substantial portion of the needle exposed for insertion into a vial or patient, this sheath, after needle use and withdrawal of the needle from the patient, manipulated so that said sheath is advanced and a cap portion is moved to enclose the sharpened end of the needle, this post-injection needle sheath including:
   (a) an injection needle including a securing hub, a shank and a sharpened distal end, this hub adapted for removeable mounting on a closed end portion of a syringe;
   (b) a cap portion having a forward end wall provided with a formed through aperture sized to slide on and along the shank of said needle;
   (c) an intermediate tubular portion secured at one end to the cap portion and having an intermediate convoluted, corrugated or bellows-type configurated portion, and with the other end being secured to said needle hub or syringe during advancing movement of the cap portion, and
   (d) means for retaining said sheath in the needle-exposed condition until the attendant withdraws the needle from the patient and desires to enclose the sharpened end of the needle.

2. A post-injection needle sheath as in claim 1 in which the cap portion is provided with means for removeable mounting on said cap portion of a needle shield, therewith providing protection of an exposed portion of said needle prior to insertion and other use.

3. A post-injection needle sheath as in claim 1 in which the cap portion has means for limiting the forward movement of the cap portion as and when the sharpened end of the needle is within the cap portion.

4. A post-injection needle sheath as in claim 2 in which the cap portion is integrally formed to provide a shoulder sized to removeably retain the needle shield and to provide an outwardly-extending flange providing a manipulating means for the attendant to move the cap portion forwardly and cause the corrugated-bellows portion to be extended, this bellows portion in an extended position limiting the forward position of the cap portion.

5. A post-injection needle sheath as in claim 4 in which the tubular portion extending rearwardly from the corrugated-bellows portion is sized to be and is secured to the needle hub.

6. A post-injection needle sheath as in claim 5 in which the corrugated-bellows portion is of plastic and, in the expanded condition, has a memory tending to urge the cap portion toward the needle hub.

7. A post-injection needle sheath as in claim 5 in which the cap portion, flange, corrugated-bellows portion and the rearward tubular portion are of a unitary molding of plastic.

8. A post-injection needle sheath as in claim 5 in which the cap portion is of a separate material having at least partially resilient properties promoting the imbedding of the sharpened end of the needle in an inner end wall of the cap portion after sheath extension to enclose the needle.

9. A post-injection needle sheath as in claim 1 in which the tubular portion extending rearwardly from the corrugated-bellows portion is sized to be and is secured to the extending needle-hub retaining portion of a syringe.

10. A post-injection needle sheath as in claim 9 in which the needle-hub retaining portion of the syringe is formed to provide a luer lock arrangement and the hub of the needle is provided with a compatible luer lock mounting means.

11. A post-injection needle sheath as in claim 1 in which the needle hub is conventionally formed with flutes and the cap portion is also formed with internal flutes adapted to mate with and slide by the flutes as formed on the needle hub, these flute portions, when in meshed condition and with the sheath in the compact condition, providing means for manipulating, rotating and mounting the needle hub and sheath on the closed end of the syringe.

12. A post-injection needle sheath as in claim 11 in which the rearwardly-extending portion of the corrugated-bellows portion is sized to be secured to the needle hub rearward of the formed flutes.

13. A post-injection needle sheath as in claim 1 in which the inner wall of the cap portion is formed with a protruding portion around the through aperture, this protruding portion providing a deflecting means for the sharpened end of the needle.

14. A method for constructing, mounting and using a post-injection needle sheath particularly adapted for enclosing the sharpened end of a needle as used with a syringe, the needle in the originally presented condition having the sheath portion in a compact condition, with a substantial portion of the needle exposed for insertion into a vial or patient, this sheath, after needle use and withdrawal of the needle from the patient, manipulated so that said sheath is advanced, moving the forward cap portion so as to go beyond the sharpened end of the needle and enclose said sharened end, this method including the steps of:
   (a) mounting an injection needle including a securing hub, a shank and a sharpened distal end, this hub adapted for removeable mounting on a closed end portion of a conventionally selected syringe;
   (b) forming and providing a cap portion having a forward end wall in which is formed on through aperture sized to slide on and along the shank of said needle;

(c) providing and securing one end of an intermediate tubular portion to the cap portion and having said intermediate portion convoluted to form a corrugated, bellows-like configurated portion, with the other end secured;

(d) limiting the forward movement of the cap portion as and when the sharpened end of the needle is within the cap portion so as to enclose said sharpened end to prevent accidental pricking, and (e) retaining said sheath in needle-exposed condition until the attendant withdraws the needle from the patient and desires to enclose the sharpened end of the needle.

15. A method for constructing, mounting and using a post-injection needle sheath as in claim 14 which further includes forming the cap portion with a shoulder sized and shaped for removeably retaining a needle shield, and providing with this cap portion an outwardly-extending flange providing a manipulating means for the attendant to move the cap portion forwardly and cause the corrugated-bellows portion to be extended, this bellows portion in an extended position limiting the forward position of the cap portion.

16. A method for constructing, mounting and using a post-injection needle sheath as in claim 14 which further includes sizing that tubular portion of the corrugated-bellows portion for securing said tubular portion to the needle hub.

17. A method for constructing, mounting and using a post-injection needle sheath as in claim 14 which includes forming the cap portion of a separate material having at least partially resilient properties promoting the imbedding of the sharpened end of the needle in an inner end wall of the cap portion after sheath extension to enclose the needle.

18. A method for constructing, mounting and using a post-injection needle sheath as in claim 14 which further includes forming the needle hub with conventionally configured flutes and with the cap portion also formed with internal flutes adapted to mate with and slide by the flutes as formed on the needle hub, these flute portions, when in meshed condition and with the sheath in the compact condition, providing means for manipulating, rotating and mounting the needle hub and sheath on the closed end of the syringe.

19. A method for constructing, mounting and using a post-injection needle sheath as in claim 14 which further includes forming the inner wall of the cap portion with a protruding portion around the through aperture, this protruding portion providing a deflecting means for the sharpened end of the needle.

20. A method for constructing, mounting and using a post-injection needle sheath as in claim 14 which further includes sizing that tubular portion of the corrugated-bellows portion for securing said tubular portion to the reduced end portion of a syringe.

* * * * *